United States Patent [19]

Sayles

[11] Patent Number: 5,429,804
[45] Date of Patent: Jul. 4, 1995

[54] ONE-STEP TESTING DEVICE

[76] Inventor: Philip W. Sayles, 172 Sycamore St., Watertown, Mass. 02172

[21] Appl. No.: 275,256

[22] Filed: Jul. 15, 1994

[51] Int. Cl.⁶ .............................................. G01N 21/01
[52] U.S. Cl. ..................................... 422/58; 422/61; 422/68.1; 422/102; 128/771; 604/404
[58] Field of Search ................... 422/58, 61, 102, 68.1; 128/771; 604/318, 404

[56] References Cited

U.S. PATENT DOCUMENTS

| | | | |
|---|---|---|---|
| 4,237,234 | 2/1980 | Meunier | 422/61 X |
| 4,473,530 | 9/1984 | Villa-Real | 422/61 X |
| 4,518,565 | 5/1985 | Boger et al. | 422/58 |
| 4,976,923 | 12/1990 | Lipsky et al. | 422/61 X |
| 5,069,878 | 12/1991 | Ehrenkranz | 422/61 |
| 5,119,830 | 6/1992 | Davis | 422/61 X |

Primary Examiner—Jeffrey R. Snay
Attorney, Agent, or Firm—William Nitkin

[57] ABSTRACT

A testing device having a lower cup for receipt of a fluid specimen and a lid containing a chamber having one or more reagent strips protruding therefrom, such reagent strips having color change testing areas thereon. The lid is attachable to the cup with the device to be inverted for the fluid specimen to reach the protruding reagent strips and for the device to be set upright for the reading of the color change testing areas through a transparent area of the lid.

8 Claims, 2 Drawing Sheets

ONE-STEP TESTING DEVICE

BACKGROUND OF THE INVENTION

1. Field of the Invention

The device of this invention resides in the area of structures for the conducting of chromatographic immunoassay testing of fluids on reagent-containing membrane strips and more particularly relates to a test container holding the fluid to be tested to accomplish one or a plurality of tests while the container is in a closed state.

2. Description of the Prior Art

Triage assay testing of bodily fluids is well known but has the serious disadvantage of requiring the tester to be exposed to contact with bodily fluids, such as urine, during the pipetting step. Such tests are slow, multi-step procedures which are difficult to carry out in hectic environments such as hospital emergency rooms.

In the prior art is Lipsky U.S. Pat. No. 4,976,923 et al which patent discloses a specimen cup with a cover wherein the fluid to be tested is first placed in the specimen cup. The cover is positioned on the cup, and the closed cup is inverted so that the fluid can pass into apertures in the cover assembly where it reacts with a reagent therein to cause different color reactions which display the analytical characteristics of the fluid being tested. Such a specimen cup structure has great advantages in today's health environment where bodily fluids may contain dangerous viruses such as AIDS and the like. Health workers do not want to endanger their health by coming in direct physical contact with such fluids but still wish to perform necessary tests safely. In some cases the sealing of the fluids within such a specimen cup can be done by the person whose fluids are being tested. For example, in urine testing the subject whose fluids are to be tested would urinate into the specimen cup and would then place the cover on the cup, sealing the urine in the cup. Therefore the lab technician performing the test need not open the cup or come in direct contact with the bodily fluids contained in the specimen cup. Thus a specimen cup which can be sealed during testing has a significant advantage over the open fluid testing procedures of the past.

SUMMARY OF THE INVENTION

It is a goal of this invention to provide an improved closed specimen cup testing system utilizing a lid containing at least one reagent membrane strip for the conducting of at least one test which will more efficiently perform chromatographic immunoassay testing.

The structure of this invention in one embodiment provides a cup, a cover lid, a chamber disposed beneath the lid, and a plurality of reagent membrane strips, hereinafter called reagent strips, arrayed within the chamber. The reagent strips extend through notches formed in the side wall of the chamber and protrude into an area where they can come in contact with the fluid to be tested beneath the cover lid when the cup is inverted. The reagent strips are visible through a transparent top in the cover lid. In use, when the fluid specimen is placed within the specimen cup and the lid is affixed in fluid-tight relationship thereon by screw threads or other attachment means, the specimen cup is inverted, allowing the fluid to be tested to come in contact with the ends of each reagent strip which protrude beyond the chamber side wall beneath the cover lid. Each reagent strip is disposed within its own chamber segment within the chamber. The fluid is drawn along each reagent strip by capillary action until the fluid comes to the bands of the chromatographic immunoassay test reagent where a color change can occur when each strip reacts with the fluid to perform the desired test. Very small amounts of the fluid sample are carried by capillary action from the protruding end of each reagent strip along the length of the reagent strip. The transparent top of the lid allows each reagent strip to be observed for color change reactions, and labels around the rim at the top of the lid disclose which reagent strip is performing which test in its associated chamber segment.. Thus, if desired, multiple tests utilizing the same fluid specimen can be performed at one time. The testing device of this invention combines all the advantages of a closed system test for fluids, such as urine and the like, and allows for more efficient multiple tests to be performed on the same fluid specimen.

DESCRIPTION OF THE PREFERRED EMBODIMENT(S)

Figure 1:
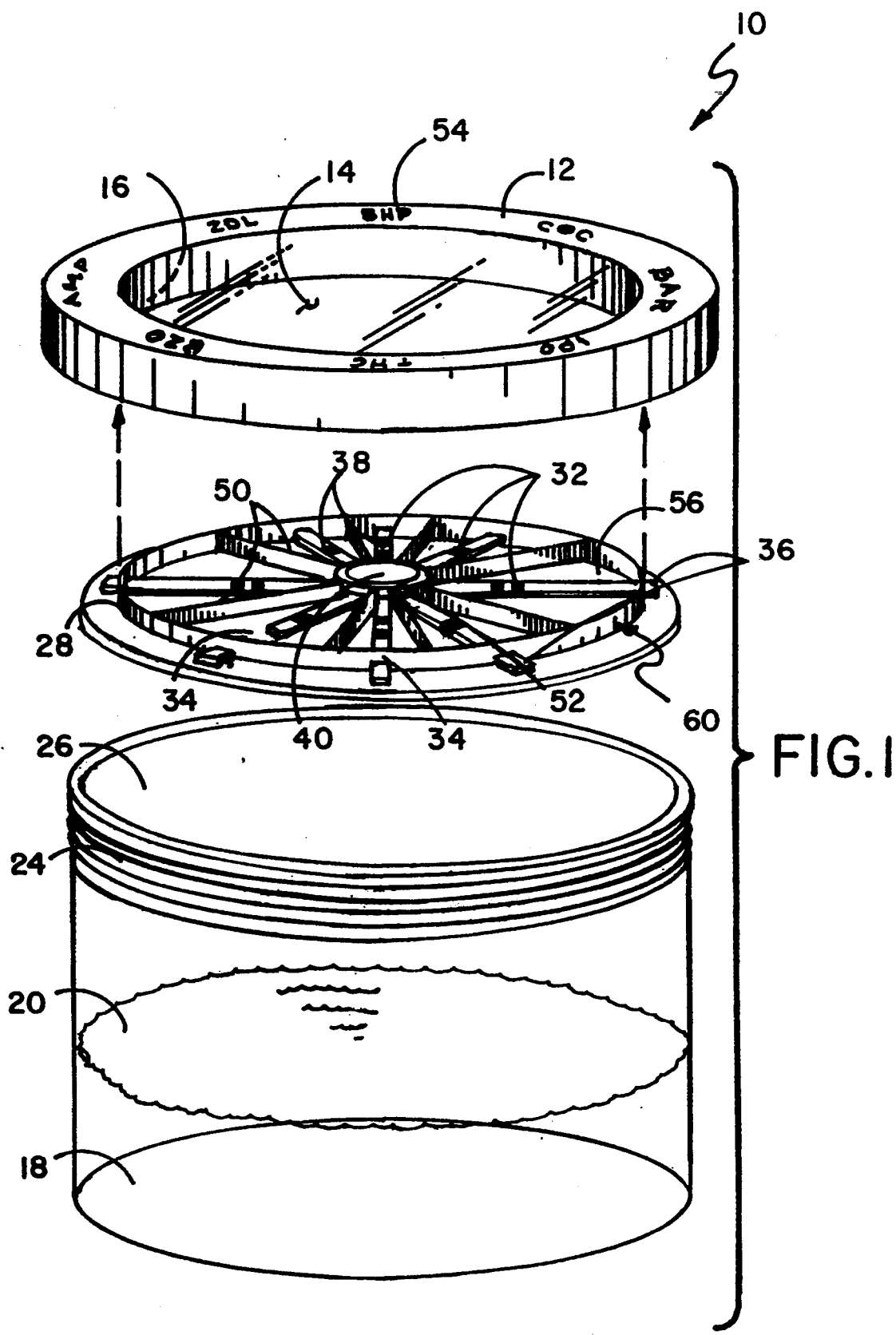
FIG. 1 illustrates a perspective, spread-apart view of one embodiment of the testing device of this invention showing its component parts.
Figure 2:
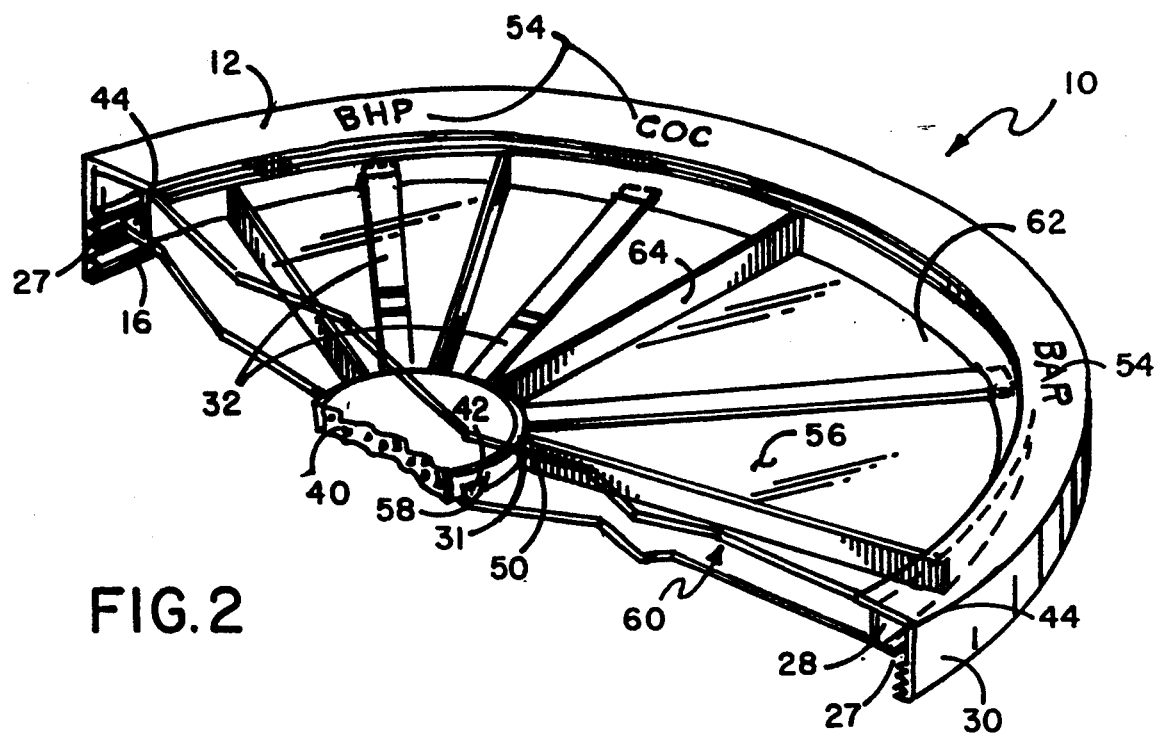
FIG. 2 illustrates a perspective, cross-sectional view of one embodiment of the testing device showing a portion of the cover lid having a chamber with a plurality of chamber segments disposed therein.

FIG. 1 illustrates the fluid testing device of this invention showing cup 18 containing fluid 20 to be tested. Fluid 20 to be tested is deposited through cup opening 26 into the cup. In one embodiment if the fluid is urine, the person whose fluid is to be tested could urinate directly into the cup. Threads 24 are disposed at the outer top of cup 18 which threads interengage in fluid-tight relationship with mating threads 16 disposed on lid 10 seen thereabove. Other means of fluid-tight attachment of the lid to the cup can be used as long as they securely hold the lid onto the cup when the testing device is inverted for the fluid to contact protruding ends 36 of reagent strips 32, as described below. Lid 10 has a transparent central area 14 and rim 12 extending around the transparent area on which rim can be written a plurality of indicia 54 to indicate the particular test being done in the chamber segment 62, seen in FIG. 2, directly below indicia 54. Also seen in FIG. 2 is chamber 60 having chamber bottom 56 and chamber side wall 28, the top of which is permanently affixed to the bottom of lid 10 generally under rim 12, leaving a space 27 between chamber side wall 28 and side 30 of lid 10. Along the bottom of chamber side wall 28 are a plurality of shallow, flat, elongated openings forming notches 34 in which are positioned in mating relationship the protruding ends 36 of reagent strips 32 which protruding ends of the reagent strips extend beyond chamber side wall 28 and totally fills notches 34, thereby closing any openings into chamber 60.

Figure 3:
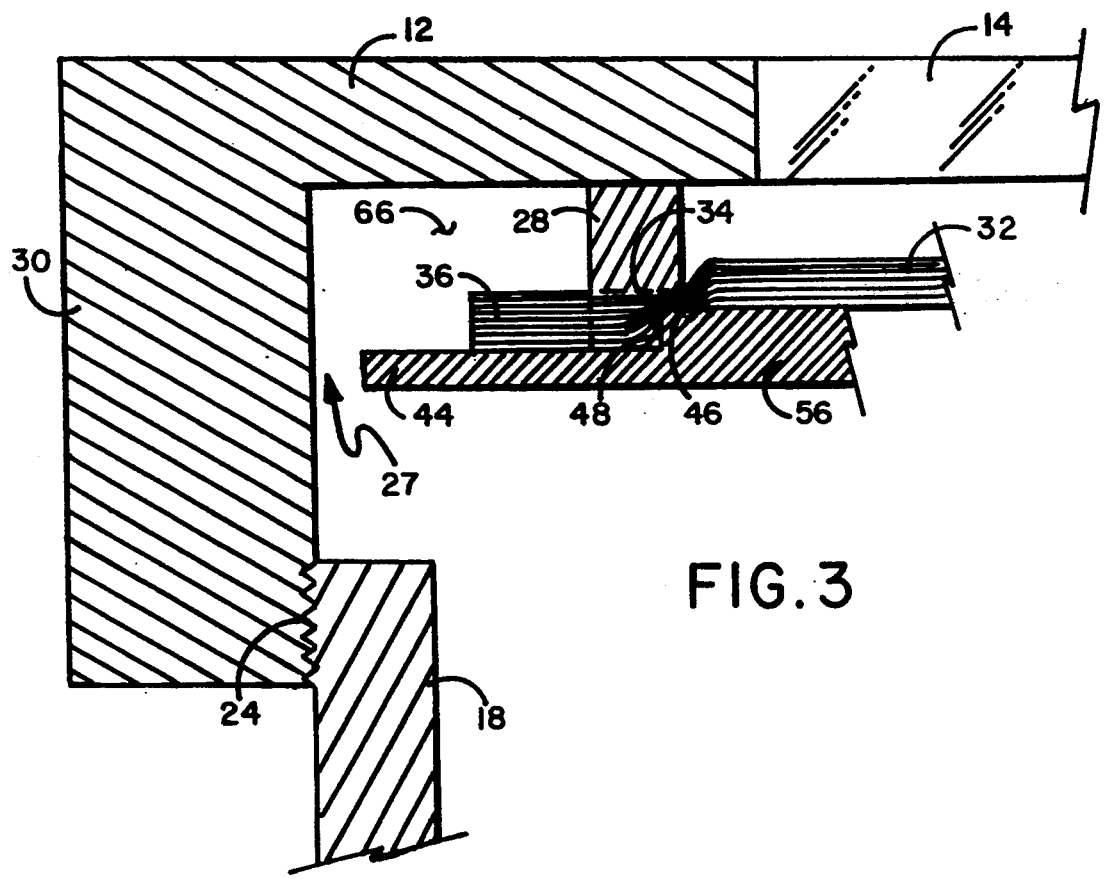
FIG. 3 illustrates a cross-sectional view of an edge portion of the lid and chamber.

Chamber bottom 56, as seen in FIG. 3, in one embodiment has a mating junction 48 with the bottom of chamber side wall 28 to aid in aligning chamber bottom 56 when attaching it to the bottom of chamber side wall 28. Further, chamber bottom 56 has a portion thereof extending outward around its perimeter under protruding end 36 to form splash shield 44 which serves to protect protruding end 36 of reagent strip 32 from inadvertent splashes of the fluid being tested. Sufficient fluid must contact protruding end 36 in reagent strip fluid contact area 66 to properly perform the tests. The use of splash shield 44 allows protruding end 36 to be contacted by the fluid only upon the inversion of cup 18 with lid thereon, and such contact is then with sufficient fluid for a sufficient time period. Even though chamber bottom 56 tends to compress reagent strip 32 at the end of notch 34, as seen at compression area 46, the fluid still moves along reagent strip 32 by capillary action.

As seen in FIG. 2, each reagent strip 32 is positioned within a single chamber segment 62 in chamber 60. Each chamber segment 62 has two, substantially vertical chamber divider walls 50, as seen also in FIG. 2, such that the reagent strip is positioned within the chamber side wall notch 34 and extends from beyond chamber side wall 28, in one embodiment, to central absorption pad 40 held within central absorption pad wall 58. A plurality of notches 42 are defined in central absorption pad wall 58, each of a size to receive and hold an interior end portion 31 of a reagent strip in mating relation thereto. Central absorption pad 40 is in contact with interior end portions 31 of the reagent strips and aids in drawing fluid by capillary action from protruding ends 36 of reagent strips 32 beyond chamber side wall 28 when contacted with fluid 20 from cup 18 when cup 18 is inverted such that the fluid reaches color change area 38, seen in FIG. 1, on the reagent strip where each testing reaction occurs. The colorimetric changes showing the test results can be observed through transparent window 14 with each reagent strip identified by test indicia 54 which indicates which test is being performed by the particular reagent strip that is located immediately below indicia 54, as seen in FIG. 2. It should be noted that notches 34 in chamber side wall 28 and notches 42 in central absorption pad wall 58 are completely filled by the reagent strips so that no fluid directly flows into any chamber segment 62. Thus the individual chamber segments form divided reaction zones, each isolated from the adjacent-positioned reaction zone by chamber segment dividers 64 to prevent any transference of any reagents from one test strip to the other. The centrally positioned absorption pad 40 into which the interior ends of the reagent strips extend through notches 42 in central absorption pad wall 58 picks up and retains any excess fluid sample that may pass along the reagent strips and in some cases may further aid in the interior movement of the fluid to be tested along each reagent strip.

Although cup, lid and chamber of this invention are illustrated as being round and having a circular cross-section, other shaped components could also be used in the device of this invention.

The testing device of this invention allows multiple testing of fluids or other items to be tested to occur within a closed unit and provides significant advantages over the prior art. The use of the transparent viewing area through the sealed lid is a significant advance over the prior art which required a nomogram to attempt to analyze a difficult-to-analyze color change.

Although the present invention has been described with reference to particular embodiments, it will be apparent to those skilled in the art that variations and modifications can be substituted therefor without departing from the principles and spirit of the invention.

I claim:

1. An improved testing device having a testing mode, said device for receipt of a fluid specimen to be tested being of the type having a cup with a lid, said lid having a top, a bottom surface of said top, a top perimeter and a lid side wall, said lid able to be attached to said cup in fluid-tight relationship, comprising:
   a chamber having a bottom and a side wall, said chamber side wall disposed in contact with said bottom surface of said lid top within and spaced away from said lid side wall defining a space therebetween, said space between said chamber and said lid defining a reagent strip fluid contact space, said chamber side wall having at least one notch defined therein;
   said lid's top being transparent; and
   a reagent strip having a length, a first end portion and a second end portion, said reagent strip having a color change testing area disposed along its length disposed under said transparent top of said lid, said second end portion extending through said notch in said chamber side wall and into said reagent strip fluid contact space, said device in its testing mode with a fluid specimen contained within said cup and said lid attached thereto, to be inverted, causing said fluid to flow into said reagent strip fluid contact space and come in contact with said second end portion of said reagent strip and causing a change of color in said color change testing area which test result can be viewed through said transparent top of said lid.

2. The device of claim 1 further including:
   a plurality of said reagent strips, each having a color change area disposed along its length, and each having a first end portion and a second end portion; and
   a plurality of substantially vertical chamber divider walls arrayed within said chamber extending from said bottom surface of said lid's transparent top to said chamber's bottom, said chamber divider walls each having an end, said ends in contact with said chamber side wall and forming a plurality of chamber segments in conjunction with said bottom surface of said transparent top, said chamber side wall and said chamber bottom, one of said reagent strips associated with a single chamber segment, the portion of each chamber side wall between two adjacent chamber divider walls having a notch defined therein for said second end portion of one of said plurality of reagent strips to extend therethrough to said reagent strip fluid contact space.

3. The device of claim 2 wherein said chamber side wall has a top and a bottom having a perimeter, said bottom of said chamber side wall being attached to said chamber bottom and said top of said chamber side wall being affixed to said lid; and
   wherein said notches are defined at said bottom of said chamber side wall, each of said notches being shallow, flat, elongated openings corresponding in shape to said shape of said second end portion of said reagent strips, said second end portion of one of said reagent strips passing through one of said notches, filling said opening and being disposed in said reagent strip fluid contact space between said chamber side wall and said lid side wall.

4. The device of claim 3 wherein said chamber bottom extends laterally around its perimeter to form a splash shield under said second end portions of said reagent strips passing through said notches and into said reagent strip fluid contact space.

5. The device of claim 3 further including indicia imprinted on said top perimeter of said lid above each chamber segment to identify the test being done by said reagent strip in said chamber segment.

6. The device of claim 5 wherein said cup and lid are circular in cross-section and said lid, when said device is in its testing mode, being screwably attached to said cup.

7. The device of claim 5 further including an absorption pad centrally disposed within said chamber, said absorption pad in fluid communication with each of said first end portions of said reagent strips.

8. The device of claim 7 further including an absorption pad wall surrounding said absorption pad which wall has defined therein a plurality of apertures, each of said apertures receiving one of said first end portions of said reagent strips; and wherein said first ends of said plurality of chamber divider walls contact said absorption pad wall.

* * * * *